United States Patent
Dvori Levy et al.

(10) Patent No.: US 12,163,106 B2
(45) Date of Patent: Dec. 10, 2024

(54) METHOD OF EXTRACTING POLYHYDROXYLATED FATTY ALCOHOLS USING SUPERCRITICAL $CO_2$

(71) Applicant: AVOMED LTD., Rosh Pina (IL)

(72) Inventors: Yael Dvori Levy, Ramat Gan (IL); Oded Bashan, Rosh Pina (IL); Ohad Bashan, Sde Varburg (IL)

(73) Assignee: AVOMED LTD., Rosh Pina (IL)

( * ) Notice: Subject to any disclaimer, the term of this patent is extended or adjusted under 35 U.S.C. 154(b) by 230 days.

(21) Appl. No.: 17/614,353

(22) PCT Filed: May 18, 2020

(86) PCT No.: PCT/IL2020/050542
§ 371 (c)(1),
(2) Date: Nov. 25, 2021

(87) PCT Pub. No.: WO2020/240537
PCT Pub. Date: Dec. 3, 2020

(65) Prior Publication Data
US 2022/0220411 A1 Jul. 14, 2022

(30) Foreign Application Priority Data
May 29, 2019 (IL) .......................................... 266991

(51) Int. Cl.
*C11B 1/10* (2006.01)
*B01D 11/02* (2006.01)

(52) U.S. Cl.
CPC .......... *C11B 1/104* (2013.01); *B01D 11/0203* (2013.01); *B01D 11/028* (2013.01); *B01D 11/0288* (2013.01); *B01D 11/0296* (2013.01)

(58) Field of Classification Search
CPC ....... C11B 1/104; C11B 1/10; B01D 11/0203; B01D 11/028; B01D 11/0288;
(Continued)

(56) References Cited

U.S. PATENT DOCUMENTS 9,982,216 B2 * 5/2018 Segal ..................... A61K 8/375
2011/0217251 A1 9/2011 Meretzki et al.
(Continued)

FOREIGN PATENT DOCUMENTS

CN 1488739 A 4/2004
CN 104321067 A 1/2015
(Continued)

OTHER PUBLICATIONS

Cachon et.al, Gases in Agro-Food Processes, Chapter 7.7 "Supercritical Fluid Applications in the Food Industry" pp. 483-509, published by Elsevier Inc., https://doi.org/10.1016/B978-0-12-812465-9.00020-7 (Jan. 2019).
(Continued)

Primary Examiner — Deborah D Carr
(74) Attorney, Agent, or Firm — The Roy Gross Law Firm, LLC; Roy Gross

(57) ABSTRACT

A method of extracting Polyhydroxylated Fatty Alcohols is disclosed. The method may include: inserting crushed avocado seeds to one or more extraction chambers; flowing supercritical $CO_2$ fluid through the crushed avocado seeds in one or more extraction chambers; and separating from the supercritical $CO_2$ flown through the crushed avocado seeds the Polyhydroxylated Fatty Alcohols extracted and dissolved in the supercritical $CO_2$. The supercritical $CO_2$ fluid may be the only solvent used for dissolving and extracting the Polyhydroxylated Fatty Alcohols.

6 Claims, 2 Drawing Sheets

(58) Field of Classification Search
CPC ...... B01D 11/0296; A23D 9/02; A61K 8/345; A23L 19/00; A23L 19/07
See application file for complete search history.

(56) References Cited

U.S. PATENT DOCUMENTS

| | | | |
|---|---|---|---|
| 2011/0250154 | A1 | 10/2011 | Meretzki et al. |
| 2015/0175933 | A1 | 6/2015 | Segal et al. |

FOREIGN PATENT DOCUMENTS

| | | | |
|---|---|---|---|
| CN | 107629868 | A | 1/2018 |
| CN | 110791376 | A | 2/2020 |
| EP | 2802335 | A1 | 11/2014 |
| WO | 2007029264 | A2 | 3/2007 |
| WO | 2011059170 | A2 | 5/2011 |

OTHER PUBLICATIONS

Neeman et al.: "New Antibacterial Agent Isolated from the Avocado Pear", Applied Microbiology, vol. 19, No. 3, Mar. 1, 1970 (Mar. 1, 1970), pp. 470-473, XP093120354, US, ISSN: 0003-6919, D01: 10.1128/am. 19.3.470-473.1970.

Eikani, M.H., Goodarznia, I. and Mirza, M. (1999), Supercritical carbon dioxide extraction of cumin seeds (*Cuminum cyminum* L.). Flavour Fragr. J., 14: 29-31. https://doi.org/10.1002/(SICI)1099-1026(199901/02)14:1<29::AID-FFJ765>3.0.CO;2-G.

Follegatti Romero, Luis & Piantino, Carla & Grimaldi, Renato & Cabral, Fernando. (2009). Supercritical CO2 extraction of omega-3 rich oil from Sacha inchi (*Plukenetia volubilis* L.) seeds. The Journal of Supercritical Fluids. 49. 323-329. 10.1016/j.supflu.2009.03.010.

Friedrich, J.P., Pryde, E.H. Supercritical CO2 extraction of lipid-bearing materials and characterization of the products. J Am Oil Chem Soc 61, 223-228 (1984). https://doi.org/10.1007/BF02678773.

Fiori L. Supercritical extraction of sunflower seed oil: experimental data and model validation. The Journal of Supercritical Fluids. Oct. 1, 2009;50(3):218-24 https://doi.org/10.1016/j.supflu.2009.06.011.

Mezzomo N, Mileo BR, Friedrich MT, Martinez J, Ferreira SR. Supercritical fluid extraction of peach (*Prunus persica*) almond oil: process yield and extract composition. Bioresour Technol. Jul. 2010; 101(14):5622-32. doi: 10.1016/j.biortech.2010.02.020. Epub Mar. 3, 2010. PMID: 20202828.

PCT International Search Report for International Application No. PCT/IL2020/050542, mailed Jun. 30, 2020, 5pp.

PCT Written Opinion for International Application No. PCT/IL2020/050542, mailed Jun. 30, 2020, 3pp.

PCT International Preliminary Report on Patentability for International Application No. PCT/IL2020/050542, issued Nov. 16, 2021, 4pp.

Guo Hai-rong et al., Supercritical CO2 extraction of higher aliphatic alcohol from filter mud of sugarcane, Science and Technology of Food Industry, vol. 32, No. 09, 2011, p. 249-254.

Dai Haofu, et al., Modern separation technology of natural products, China Agricultural University, Modern Separation Technology for Natural Products, 2006. p. 193.

\* cited by examiner

METHOD OF EXTRACTING POLYHYDROXYLATED FATTY ALCOHOLS USING SUPERCRITICAL $CO_2$

CROSS REFERENCE TO RELATED APPLICATIONS

This application is a National Phase of PCT Patent Application No. PCT/IL2020/050542 having International filing date of May 18, 2020, which claims the benefit of priority of Israeli Patent Application No. 266991, filed May 29, 2019, the contents of which are all incorporated herein by reference in their entirety.

FIELD OF THE INVENTION

The present invention generally relates to a method of extracting Polyhydroxylated Fatty Alcohols. More particularly, the present invention relates to a method of extracting Polyhydroxylated Fatty Alcohols using supercritical $CO_2$.

BACKGROUND OF THE INVENTION

Polyhydroxylated Fatty Alcohols have known cosmetic and pharmaceutical benefits, for example, a significant increase in the inhibition of T-cell proliferation which may be highly helpful when treating inflammations and various pathogenic conditions, such as atopic dermatitis, contact dermatitis, rheumatoid arthritis etc. Polyhydroxylated fatty alcohols (PFA) are crystalline lipophilic molecules. PFA molecules have a long aliphatic (mostly C17) chain with one end unsaturated with a double or triple (acetylenic) bond, and the other end having three hydroxyl groups. Some of the PFA molecules are polar and the other are non-polar molecules. The polarity of the different types of PFA molecules depends on the presence of hydroxyl groups, double or triple bonds or other polar groups in the molecule. Therefore, since all known solvents are either polar (e.g., suitable for extracting polar extracts) or non-polar (e.g., suitable for extracting non-polar extracts) it is almost impossible to extract all PFA molecules using the same solvent.

Some types of PFA can be extracted form Avocado seeds, using organic solvents, for example, methanol, alkyl acetates (e.g., butyl acetate) and the like. These organic solvents are toxic and environmentally unfriendly. Therefore, any cosmetic and pharmaceutical product that includes PFA extracted using an organic solvent must be cleaned from any residual solvent.

There are three solvents that are considered toxin-free (e.g, non-toxic), water, ethanol and supercritical $CO_2$. Water and ethanol are polar solvents not suitable for extractions of oils and the non-polar PFA molecules. Supercritical $CO_2$ is intrinsically non-polar, and it is suitable solvent for extraction of non-polar compounds, such as, oil and some low molecular weight, volatile, polar compounds. However, it is less effective in the extraction of polar phytochemicals embedded in the cell wall, such as polar PFA molecules.

Furthermore, even for non-polar extracts such as oils from cursed seeds, the known practice in the field includes the addition of 7-15 wt. % of organic cosolvent, to the supercritical $CO_2$. Such an addition is known to be essential for extraction of oils from crushed seeds. Therefore, in all known commercial lines a cosolvent tank is included in the line for adding cosolvent to the supercritical $CO_2$. The added cosolvents may enhance the solvation power of supercritical $CO_2$ and improve the recovery of bioactive compounds (e.g., the diffusion of the bioactive compounds via the cells wall). This process is used for extraction of oils from crushed seeds, such as, lemon, mandarin, orange, watermelon, Cucurbita pepo, tomato and the like. The organic cosolvent, although in smaller amounts than in methods based solely on the organic cosolvent, still needs to be removed and recycled and can make the extracted oil contaminated with residual cosolvent. Any process that uses such cosolvents cannot be regarded as 100% environmentally friendly or non-toxic.

Accordingly, there is a great benefit in having a non-toxic process for extracting all molecules of PFA from avocado seeds using a single solvent.

SUMMARY OF THE INVENTION

Some aspect of the invention may be directed to a method of extracting Polyhydroxylated Fatty Alcohols. Embodiments of the method may include: inserting crushed avocado seeds to one or more extraction chambers; flowing supercritical $CO_2$ fluid through the crushed avocado seeds in one or more extraction chambers; and separating from the supercritical $CO_2$ flown through the crushed avocado seeds the Polyhydroxylated Fatty Alcohols extracted and dissolved in the supercritical $CO_2$. In some embodiments, the supercritical $CO_2$ fluid being the only solvent used for dissolving and extracting the Polyhydroxylated Fatty Alcohols.

In some embodiments, the method may further include drying the crushed avocado seeds to a humidity level of at most 20 wt. %. In some embodiments, the crushed avocado seeds may have a particle size of at most 2 mm. In some embodiments, the supercritical $CO_2$ fluid may have a temperature range of 30° C. to 80° C. In some embodiments, the supercritical $CO_2$ fluid has pressure range of 100 bar to 200 bar.

In some embodiments, flowing the supercritical $CO_2$ fluid may include: obtaining liquidized $CO_2$; increasing the pressure of the liquidized $CO_2$ to reach a required supercritical pressure; heating the pressurized liquid $CO_2$ to reach a required supercritical temperature; and inserting the supercritical $CO_2$ fluid to the one or more extraction chambers.

In some embodiments, separating the Polyhydroxylated Fatty Alcohols may include: introducing the supercritical $CO_2$ flown through the crushed avocado seeds into a separator having two or more separation stages. In some embodiments, for every kilogram (kg) of crushed avocado seeds at least 1 gram (gr) of Polyhydroxylated Fatty Alcohols is extracted and collected. In some embodiments, a time of production of at least 1gr of the Polyhydroxylated Fatty Alcohols from 1 kg of crushed avocado seeds is at most 5 hours In some embodiments, the method may further include collecting the $CO_2$ separated from the Polyhydroxylated Fatty Alcohols; and recycling the collected $CO_2$.

Some aspects of the invention may be directed to a non-toxic Polyhydroxylated Fatty Alcohols extract comprising less than 0.5 ppm cosolvent.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
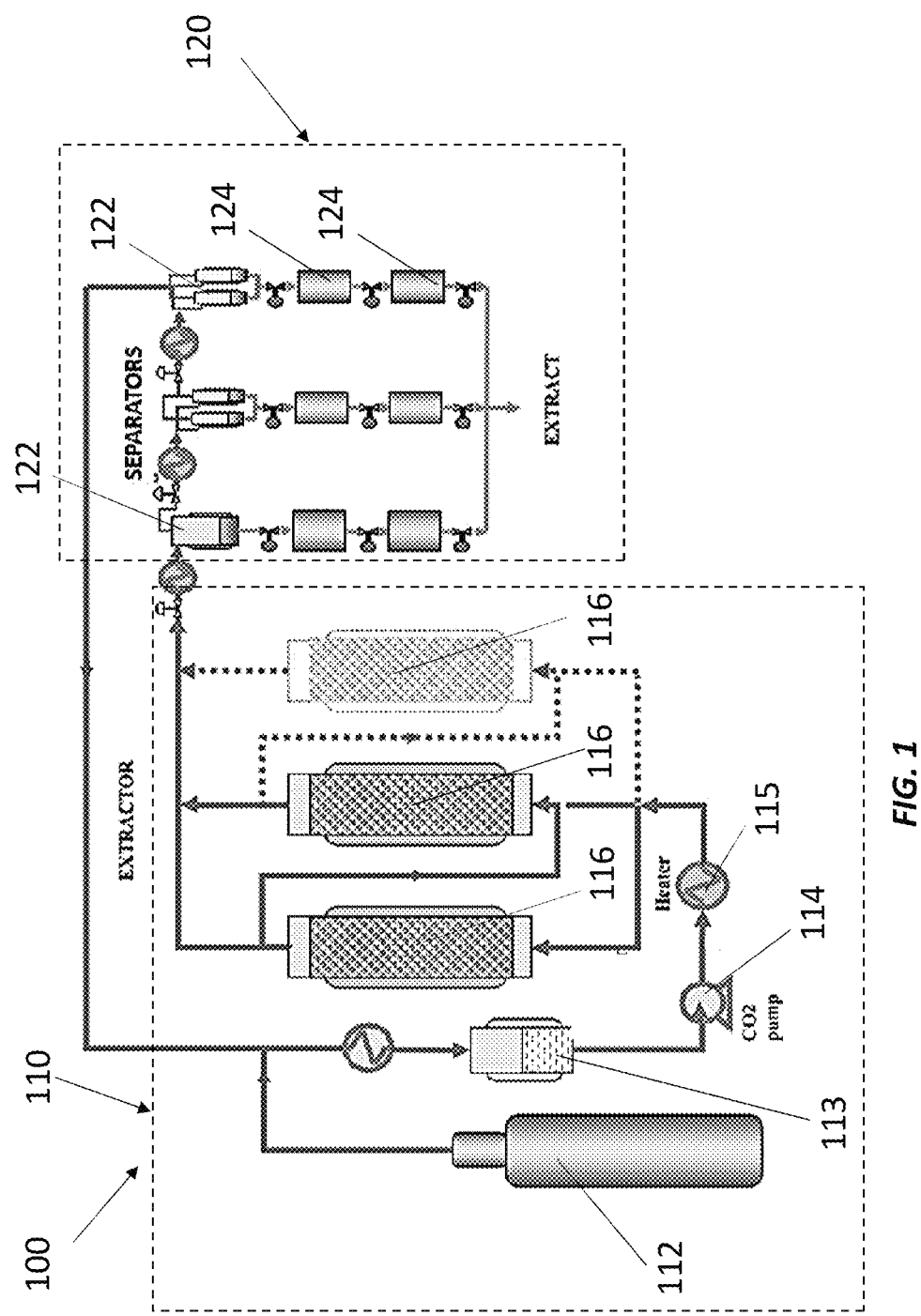
FIG. 1 is an illustration of an extraction system according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Aspects of the invention may be directed to a method of extracting all molecules of PFA, both the polar and non-polar molecules, using supercritical $CO_2$ without any additional cosolvent. Although, prior art extraction method of oils from seeds using supercritical $CO_2$ requires the addition of 7-15 wt. % of cosolvent, the applicant has surprisingly found that such an addition is not required when extracting PFA using supercritical $CO_2$ from avocado seeds, while maintaining or even increasing the required production yield. Furthermore, although supercritical $CO_2$ is known to be non-polar solvent, a method of extraction according to embodiments of the invention resulted in the extraction of both the polar and non-polar PFA molecules. Therefore, unlike the prior art methods, a method and an extract according to some embodiments of the invention may be completely non-toxic, or cosolvent free. A method according to embodiments of the invention may be executed by any known supercritical $CO_2$ extraction system, for example, the system illustrated in FIG. 1.

Referring now to FIG. 1 which is an illusration of an extraction system 100 according to some embodiments of the invention. System 100 may include an extraction unit 110 and a separation unit 120. Extraction unit 110 may include: a $CO_2$ reservoir 112 configured to hold $CO_2$, a condenser 113 configured to condense and liquidize the $CO_2$, a pump 114 (e.g., a dual piston pump) for increasing the extraction pressure of the $CO_2$ and a heater 115 for heating the pressurized $CO_2$ to supercritical conditions. Accordingly, the $CO_2$ leaving heater 115 is a supercritical $CO_2$ fluid. As used herein, supercritical $CO_2$ fluid may refer to a $CO_2$ fluid that may have a density of liquid $CO_2$ (e.g., 600-1600 kg/m$^3$) and a dissolving power (solubility) of $CO_2$ gas. In some embodiments, supercritical $CO_2$ fluid may have a temperature range of 30° C. to 80° C. In some embodiments, supercritical $CO_2$ fluid may have pressure range of 100 bar to 400 bar, for example, 100 bar to 200 bar.

In some embodiments, the supercritical $CO_2$ fluid is introduced into one or more extraction chambers 116 included in extraction unit 110. One or more extraction chambers 116 may be preloaded with crushed seeds, for example, crushed avocado seeds. The supercritical $CO_2$ fluid is flown through the crushed seeds in at least one of one or more extraction chambers 116. In some embodiments, PFA may be dissolved from the crushed seeds into the supercritical $CO_2$ fluid to form a supercritical $CO_2$ solution. In some embodiments, other materials may also be extracted from the crushed avocado seeds in the process, for example, tocopherols, carotenoids, unsaturated fatty acids, etc. It should be appreciated by those skilled in the art that a cosolvent reservoir is not required in systems according to embodiments of the present invention.

In some embodiments, the supercritical $CO_2$ solution that includes the extracted PFA may be introduced into separation unit 120 to be separated. Separation unit 120 may include one or more separators 122 each being in fluid connection to one or more tanks 124. In some embodiments, separation unit 120 may further include one or more filters and one or more containers (not illustrated) for collecting the separated PFA. In some embodiments, separators 122 may each include a tank at which the supercritical $CO_2$ solution may be depressurized using aback-pressure regulator and maintained in a desired temperature (e.g., 30-60° C.) until the $CO_2$ may gradually be converted into gas. In some embodiments, in order to avoid pressure and temperature changes the processes may be carried out is several stages in two or more separators 122. The evaporated $CO_2$ may be recycled and condensed back into a liquid $CO_2$.

It should be understood by one skilled in the art that the invention is not limited to system 100 disclosed herein and illustrated in FIG. 1, which is given as an example only.

Figure 2:
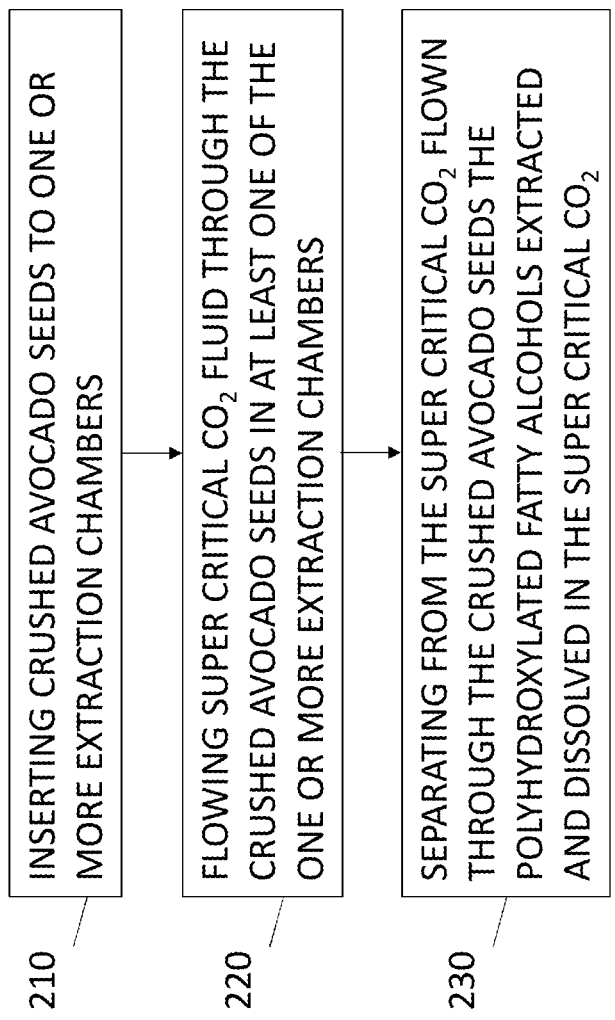
FIG. 2 is a flowchart of a method of extracting PFA using supercritical $CO_2$ according to some embodiments of the invention.

Reference is made to FIG. 2 which is a flowchart of a method of extracting PFA according to some embodiments of the invention. In step 210, crushed avocado seeds may be introduced to one or more extraction chambers (e.g., one or more chambers 116). In some embodiments, the avocado seeds may be crushed using any known method, for example, grinding, milling, etc. In some embodiments, the crushed avocado seeds may have a particle size (e.g., average diameter) of at most, 2 mm, 1 mm, 500 µm, 150 µm or less. In some embodiments, the smaller the particle size the higher is the specific surface area exposed to the supercritical $CO_2$ fluid, therefore the higher is the extraction rate of the PFA from each particle. Therefore, the smaller the particle size the higher is the yield of the extraction process.

Undried raw avocado seeds may be crushed at room temperature. In some embodiments, the crushed seeds may be dried such that the crushed seeds may have a humidity level of at most 20 wt. %, for example, at most 18 wt. %, at most 15 wt. % at most 12 wt. % or lower. PFA are insoluble in water therefore the presence of water is an impediment to the diffusion of the PFA into the supercritical $CO_2$ fluid. Furthermore, it is easier to recycle the $CO_2$ if it does not contain water.

In some embodiments, the crushed seeds may be incubated for at least 24 hours, for example, about 48 hours, at a temperature range of 15-45° C.

In step 220, supercritical $CO_2$ fluid may be flown through the crushed avocado seeds in at least one of the one or more extraction chambers (e.g., chambers 116). The supercritical $CO_2$ fluid may be obtained by pressurizing and heating $CO_2$ into supercritical conditions as disclosed hereinabove with respect to FIG. 1. Some embodiments of the invention may include: obtaining liquidized $CO_2$, increasing the pressure of the liquidized $CO_2$ to reach a required supercritical pressure and heating the pressurized liquid $CO_2$ to reach a required supercritical temperature; and inserting the supercritical $CO_2$ fluid to at least one extraction chambers.

In some embodiments, the supercritical $CO_2$ fluid may have a density of liquid $CO_2$ and a dissolving power (solubility) of the PFA in the supercritical $CO_2$ gas. In some embodiments, the supercritical $CO_2$ fluid may have a temperature range of 30° C. to 80° C. In some embodiments, the supercritical $CO_2$ fluid has pressure range of 100 bar to 400 bar, for example, 200 bar.

In some embodiments, as the supercritical $CO_2$ fluid is flowing and wetting the crushed avocado seeds, PFA may be extracted from the surface area of the crushed avocado seed particles. The PFA may be dissolved into the supercritical $CO_2$ fluid. In some embodiments, the PFA dissolved into the supercritical $CO_2$ fluid may include both polar and non-polar PFA molecules.

In step 230, PFA extracted and dissolved in the supercritical $CO_2$ may be separated from the supercritical $CO_2$ flown through the crushed avocado seeds. In some embodiments, PFA from within the avocado seed cells may diffuse from the cells and dissolve in the supercritical $CO_2$. In some embodiments, the supercritical $CO_2$ fluid may be the only solvent used for dissolving and extracting the PFA.

In some embodiments, the extracted PFA may be non-toxic and/or cosolvent free extracted PFA including both polar and non-polar PFA molecules. As used herein, the term non-toxic refers to cosolvent amounts which are lower than the required standard (e.g., lower than 20 ppm) or the lowest detection limit, for example, lower than 0.5 ppm, lower than 0.1 ppm or lower than 0.06 ppm measured, for example, using Headspace Gas Chromatograph (HSGC). In some embodiments, the lowest detection limit may depend form the type of product material (oil, paste, solid, solution, etc.), the type of the toxic cosolvent and the like.

In some embodiments, for every kg of crushed avocado seeds at least 1-gram, for example, at least 1.4-gram, 1.5-gram, 2-gram, 3-gram or more. of the PFA may be extracted and collected. In some embodiments, a time of production of at least 1 gram of the PFA from 1 kg of crushed avocado seeds may be at most 5 hours.

Experimental Results

Three batches of 2-4.5 kg of crushed avocado seeds were inserted into extraction chambers, such as chambers 116. Each batch was exposed to 8 kg of flowing supercritical $CO_2$ fluid having pressure of: 100, 350 and 450 bar at 45° C. No additional cosolvent was used in the process. The flowing rate of the supercritical $CO_2$ fluid was 21-25 kg/hour. Table 1 summarized the results of obtained PFA.

TABLE 1

| Batch No. | 1 | 2 | 3 |
|---|---|---|---|
| Avocado species | Reed | Hass | Pinkerton |
| Weight of crushed seeds [Kg] | 2.02 | 4.5 | 3.2 |
| Moisture content | 8-12% | 8-12% | 8-12% |
| Total production time | 4 h | 4 h | 4 h 35 min |
| Total quantity of PFA extraction ** | 26.0 gr | 65.1 gr | 53.0 gr |
| Total Production Yield (%, dry weight) | 1.3% | 1.4% | 1.7% |

** PFA extraction may include PFA (e.g., 10-40 wt. %) and other additives, such as, tocopherols, carotenoids and unsaturated fatty acids. The PFA included both polar and non-polar PFA molecules.

As known in the art the typical production yield of solvents (e.g., ethyl acetate, hexane, etc.) based extraction process is 0.6-0.8%. As clearly shown in Table 1 above, a process according to embodiments of the invention may result in a higher production yield without the use of any cosolvent.

Using the same raw material as in the previous experiments, additional five batches of 10-15 kg and 2 batches of 87-92 kg of crushed avocado seeds were inserted into extraction chambers, such as chambers 116. Small scale batches were exposed to 115-430 kg of flowing supercritical $CO_2$ fluid and Large-scale batches were exposed to 1,350 kg of flowing supercritical $CO_2$ fluid, having pressure of: 100, 120, 160 and optionally also 280 bar at 45° C. No additional cosolvent was used in the process. The flowing rate of the supercritical $CO_2$ fluid was 30-67 kg/hour for small scale batches and 430 kg/hour for large-scale batches. Table 2 summarized the results of obtained PFA.

TABLE 2

| Batch No. | 1 | | 2 | | 3 | 4 | 5 | 6 | 7 |
|---|---|---|---|---|---|---|---|---|---|
| Avocado species | Reed | | Reed | | Reed | Reed | Reed | Reed | Hass |
| Weight of crushed seeds [Kg] | 15.0 | | 13.5 | | 13.5 | 13.5 | 10.0 | 87.7 | 91.5 |
| Extraction Pressure (bar) | 100 bar | 280 bar* | 100 bar | 120 bar | 160 bar | 120 bar | 160 bar | 120 bar | 160 bar | 160 bar |
| Total quantity of PFA extraction ** | 320 g | | 295 g*** | | 227 g | 310 g | 142 g | 2.09 kg | 2.12 |

TABLE 2-continued

| Batch No. | 1 | 2 | 3 | 4 | 5 | 6 | 7 |
|---|---|---|---|---|---|---|---|
| Total Production Yield (%, dry weight) | 2.1% | 2.2% | 1.7% | 2.3% | 1.4% | 2.4% | 2.3% |

*A larger number of undesirable compounds were extracted at this stage using pressure of 280 bar
** PFA extraction may include PFA (e.g., 10-40 wt. %) and other additives, such as, sterols, tocopherols, carotenoids and unsaturated fatty acids. The PFA included both polar and non-polar PFA molecules.
***The highest percent of PFA in the extract obtained at the higher pressure.

As shows in table 2, as pressure increases the yield increases and the selectivity decreases, accordingly, more compounds are extracted which lead to a change in the appearance and odor of the whole extract. Batches that were extracted above 200 bar appear as dark green extract with an unpleasant odor and larger number of undesirable compounds (such as pigments). Higher pressure during extraction enable producing in higher yields.

Therefore, process according to embodiments of the invention is toxin-free (e.g., non-toxic) and may provide a high quality PFA, free of any possible residual toxic solvents.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method of extracting Polyhydroxylated Fatty Alcohols (PFA) comprising:
   drying the crushed avocado seeds to a humidity level of at most 12 wt. %;
   inserting crushed avocado seeds to one or more extraction chambers;
   flowing supercritical $CO_2$ fluid, at a pressure range of 100 bar to 200 bar, through the crushed avocado seeds in the one or more extraction chambers; and separating from the supercritical $CO_2$ flown through the crushed avocado seeds the PFA extracted and dissolved in the supercritical $CO_2$,
   wherein the supercritical $CO_2$ fluid being the only solvent used for dissolving and extracting the PFA from the seeds.

2. The method of claim 1, wherein the crushed avocado seeds have a particle size of at most 2 mm.

3. The method of claim 1, wherein the supercritical $CO_2$ fluid has a temperature range of 30° C. to 80° C.

4. The method of claim 1, wherein flowing the supercritical $CO_2$ fluid comprises:
   obtaining liquidized $CO_2$;
   increasing the pressure of the liquidized $CO_2$ to reach a required supercritical pressure;
   heating the pressurized liquid $CO_2$ to reach a required supercritical temperature; and
   inserting the supercritical $CO_2$ fluid to the one or more extraction chambers.

5. The method of claim 1, wherein separating the PFA comprises: introducing the supercritical $CO_2$ flown through the crushed avocado seeds into a separator having two or more separation stages.

6. The method of claim 1, further comprising: collecting the $CO_2$ separated from the PFA; and recycling the collected $CO_2$.

* * * * *